US00PP23565P2

(12) United States Plant Patent
Meyer

(10) Patent No.: US PP23,565 P2
(45) Date of Patent: Apr. 23, 2013

(54) ***HOSTA* PLANT NAMED 'WHEEE!'**

(50) Latin Name: ***Hosta* hybrid (Tratt.)**
Varietal Denomination: Wheee!

(76) Inventor: William J. Meyer, Woodbury, CT (US)

( * ) Notice: Subject to any disclaimer, the term of this patent is extended or adjusted under 35 U.S.C. 154(b) by 0 days.

(21) Appl. No.: 13/066,637

(22) Filed: Apr. 19, 2011

(51) Int. Cl.
*A01H 5/00* (2006.01)

(52) U.S. Cl. ..... Plt./353
(58) Field of Classification Search ..... Plt./353
See application file for complete search history.

*Primary Examiner* — Susan McCormick Ewoldt

(57) ABSTRACT

A new and distinct *Hosta* plant named 'Wheee!' characterized by light lavender flowers on strong erect scapes over broadly horizontal mounds of intensely-sinuate elliptic leaves having yellow margins, leaf blade centers of light green. Hosta 'Wheee!' emerges in the spring with distinct, broad, intensely-sinuate bracts or intermediate leaves partially clasping and surrounding emerging shoots, petioles and expanding leaves.

1 Drawing Sheet

Botanical classification: *Hosta* hybrid (Tratt.)
Variety denomination: 'Wheee!'.

BACKGROUND AND ORIGIN OF THE PLANT

The present invention relates to a new and distinct *Hosta* plant, *Hosta* 'Wheee!' hereinafter also referred to with just the cultivar name, 'Wheee!'. *Hosta* 'Wheee!' was discovered by William J. Meyer in the summer of 2004 at an unknown nursery in the New England area. 'Wheee!' is an uninduced whole plant mutation of an unknown *Hosta*. The new plant has been asexually propagated by division at the garden in Woodbury, Conn., August of 2007 with all resultant asexually propagated plants having retained all the same traits as the original plant 'Wheee!' is stable and reproduces true to type in successive generations of asexual reproduction.

There are over 4,500 registered *Hostas* with The American Hosta Society, which is the International Cultivar Registration Authority for the genus *Hosta*. The most similar *Hosta* cultivars known to the applicant are: *Hosta* 'Praying Hands' (not patented), *Hosta* 'Leola Fraim' (not patented), *Hosta* 'Honeysong' (not patented), *Hosta* 'Pineapple Punch' U.S. Plant Pat. No. 18,318. 'Praying Hands' is much more upright in habit, has narrower conduplicate foliage and darker flowers than 'Wheee!', but with sinuate foliage. 'Leola Fraim', 'Honeysong' and 'Praying Hands' all have similar yellow margins to the foliage, but both 'Leola Fraim', 'Honeysong' have flat leaves compared to the sinuate foliage of 'Wheee!'. The undulation of *Hosta* 'Pineapple Punch' is much finer and mainly on the margin compared to the coarse undulations of 'Wheee!' that goes throughout the leaf blade. 'Pineapple Punch' also has a much narrower leaf blade with more acute apex, taller scapes and darker lavender flowers. *Hosta* 'Wheee!' is the only plant known to the inventor with broad persistent bracts or intermediate leaves partially clasping and surrounding the emerging shoots that reflex or bend away in a wavy sinuate form.

*Hosta* 'Wheee!' differs from all other *Hostas* known to the applicant, by the combination of the following traits.

1. Intensely and coarsely sinuate leaf blades.
2. Elliptic leaves with yellow margins and light green center.

3. Light lavender buds opening to white flowers beginning in early July.
4. Broad persistent bracts or intermediate leaves partially clasping and surrounding emerging leaves intensely sinuate and not adpressed to shoots.

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, temperature, source and direction may cause the appearance of minor variation in color.

DETAILED BOTANICAL DESCRIPTION

Figure 1:
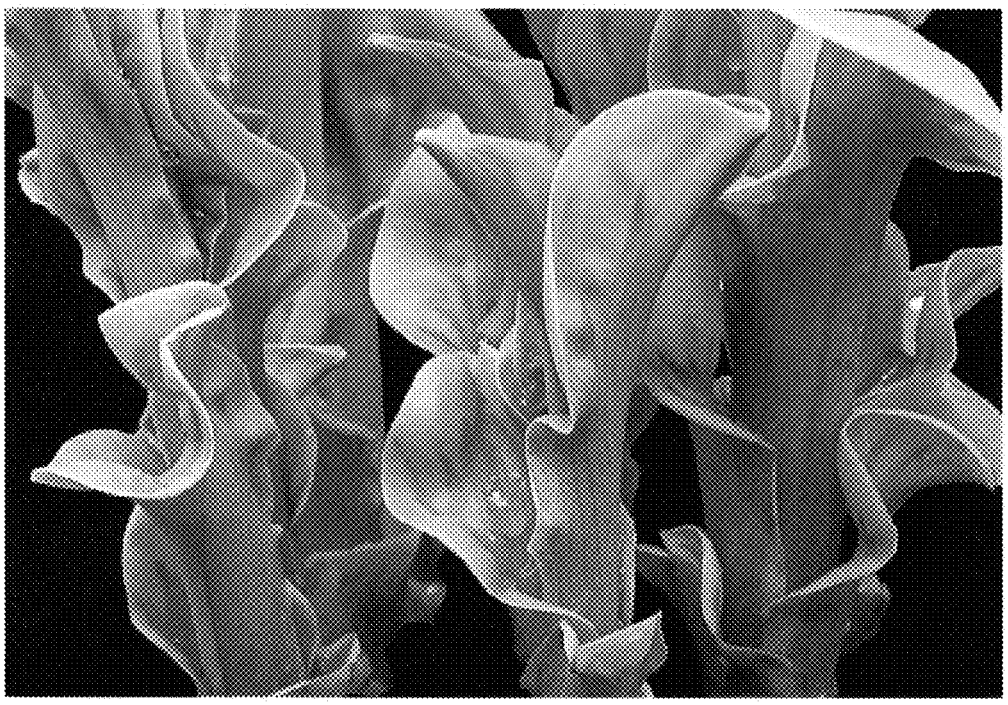
FIG. 1 shows a close-up of a two-year old plant in the landscape as it is emerging in the spring in Woodbury, Conn.
Figure 2:
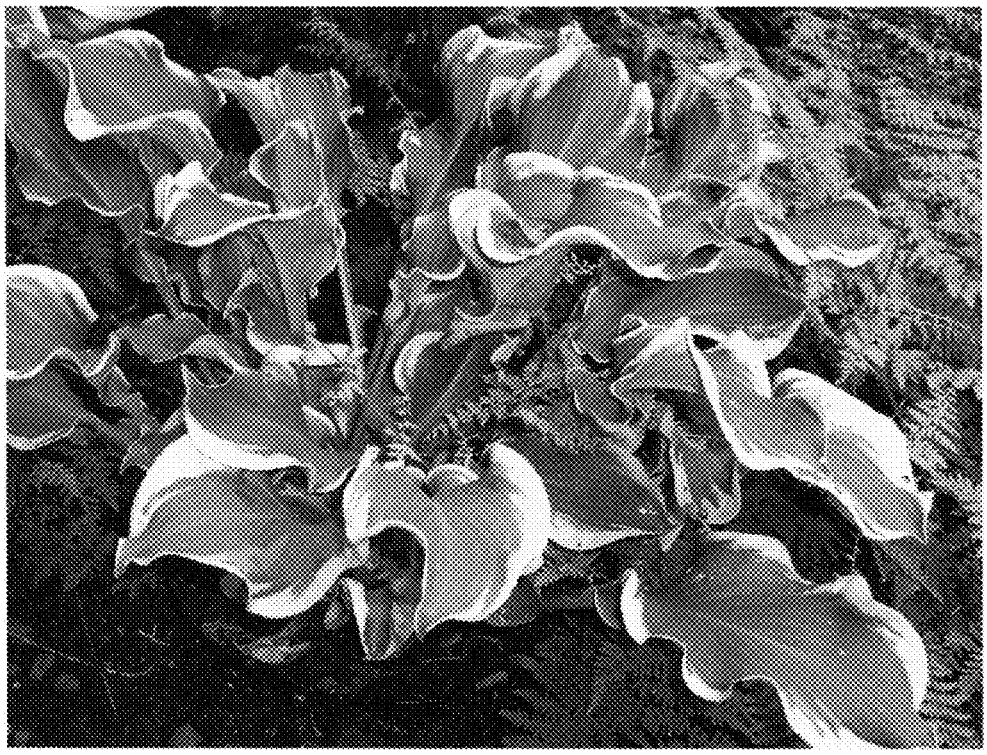
FIG. 2 shows a landscape use of a three-year old plant in mid season in Woodbury, Conn.

The following descriptions and color references are based on The 2001 edition of The Royal Horticultural Society Colour Chart except where common dictionary terms are used. The new plant, *Hosta* 'Wheee!', has not been observed under all possible environments. The phenotype may vary slightly with different environmental conditions, such as temperature, light, fertility, moisture and maturity levels, but without any change in the genotype. The following observations and size descriptions are of a potted three-year old plant in a shaded greenhouse in Zeeland, Mich. with and supplemental water and fertilizer.

Botanical classification: *Hosta*×hybrid.
Parentage: Mutation of unknown origin.
Propagation: Garden division and sterile plant tissue culture.
Time to initiate roots from tissue culture: About two to three weeks.
Growth rate: Moderate.
Crop time: About 10 to 12 weeks to finish during the summer in a one-liter container from rooted tissue culture plantlet.
Rooting habit: Fleshy, lightly branching.

Plant shape and habit: Hardy herbaceous perennial with basal rosette of leaves emerging from rhizomes producing a symmetrical mound of broadly horizontal leaves.

Plant size: Foliage height about 28 cm tall from soil line to the top of the leaves and about 75 cm wide at the widest point just above soil line.

Foliage description: Entire, glabrous, glaucous, elliptical, acute leaf apex with broadly attenuate base; coarsely sinuate; 25 to 32 cm long and 5.0 to 7.0 cm wide, average 29 cm long and 6.0 cm wide.

Bracts surrounding emerging shoot: Elliptic to ovate, with acute to rounded apex and base below ground; smaller outer bracts becoming papery and drying by about mid season; inner bracts persistent, intensely-sinuate, not adpressed to expanding shoots, leaves and petioles partially clasping and surrounding shoots, petioles and expanding leaves; varying in size with more inner bracts larger becoming more leaf-like, intensely reflexed or bent away toward the apex in a wavy sinuate form; with largest about 10 cm long and 3 cm wide and smallest about 4 cm long and 1 cm wide; coloration with variegation identical to that of leaves.

Leaf blades: Simple, entire, sinuate; bi-laterally symmetrical; glabrous and dull matte surface on top, glabrous and glaucous below; variegation pattern characteristically variable with the margin between 0.2 cm to 2.0 cm wide, generally wider with more maturity and wider at that apex and narrower at the center and base, with some jetting of margin or center color into the edge or center and intermediate colors between the leaf center and margin more pronounced at the apical on third of leaf.

Leaf blade color: Early season shortly after emergence adaxial (top) center color closest to RHS 137D; early season adaxial margin nearest RHS 144A; early season abaxial (underside) center nearest RHS N138B; early season abaxial margin nearest RHS 146D; Mid-season and later summer adaxial centers nearest RHS 137C; mid-season and later adaxial margins nearest RHS 11C; mid-season and later abaxial center nearest RHS N138C; mid-season and later abaxial margins nearest RHS 158D; intermediate colors where adaxial margin and center unevenly and irregularly fold over each other of lighter than RHS N138C, nearest RHS 148D, lighter than RHS 148D and between RHS 151B and RHS 150B; irregular intermediate abaxial colors of nearest RHS 139D, nearest RHS 145D, nearest RHS 145C and between RHS 191C and RHS 191D.

Petiole: Entire, glabrous concavo-convex; mostly straight from base of plant to leaf base with little bending or curving, stiff; 14 to 17 cm long and 8 to 12 mm wide at base, average about 16 cm long and 10 mm wide.

Petiole color: Adaxial centers nearest RHS 137C; adaxial margins nearest RHS 11C; abaxial center nearest RHS N138C; abaxial margins nearest RHS 158D.

Veins: Parallel, raised on abaxial side, normally 9 pair.

Veins color: Adaxial and abaxial veins the same color as the surrounding tissue.

Flower description:

*Buds two to three days prior to opening.*—Globose apex about 1.4 cm in diameter with base narrowing at about mid-length to about 0.4 cm diameter; about 5.5 cm long.

*Bud color.*—Light lavender lighter than RHS 84D.

*Flowers.*—Perfect; funnelform; 4.5 to 5.0 cm wide and 6.0 to 6.5 cm long, (distal flowers smaller), persists for a normal period, usually one day on plant or as cut flower; scapes remain effective with flowers from early to late July with 28 to 37 flowers per scape; no detectable fragrance.

*Tepal.*—Two sets of three, glabrous, entire; fused at base; clavate with acute apex; each approximately 6.0 cm long and the inner set 1.6 cm wide and outer set 1.4 cm wide.

*Tepal color.*—Coloring of both sets identical, light lavender inside and out nearest RHS 84D, slightly lighter on the margins.

*Tepal veins.*—Three main veins, indistinct; vein color the same color as surrounding tissue on both outer and inner surfaces.

*Gynoecium.*—Style: single, approximately 7.0 cm long, 1 mm diameter, curled upward sharply to about 90 degrees in the distal 1.5 cm; lighter than RHS 155D; Stigma: globose, about 2 mm in diameter, between RHS 155D and RHS 157D.

*Androecium.*—Filaments: six, approximately 5.0 cm long and less than 1 mm in diameter; curved upward to nearly 90 degrees in the apical 1.0 cm; lighter than RHS 155D; Anthers: 4 to 5 mm long, 1.5 mm wide, dorsifixed, dehiscent longitudinally; between RHS N187C and RHS N187D. Pollen: elliptic, less than 0.1 mm long, closest to RHS 14C.

*Peduncle.*—Usually one per mature division; glaucous, glabrous; nearly vertical to slightly bent; 85 to 90 degrees from horizontal, more horizontal with more single directional lighting; 90 to 100 cm tall, and up to 10 mm in diameter at base; nearest RHS 138B in the lower portion and nearest RHS 138D in the upper portion.

*Pedicel.*—Approximately 15 mm long, 2 mm wide; nearest RHS N138D with the distal portion slightly tinted with nearest RHS N77D.

*Scape bracts.*—Each flower usually subtended by a single bract, decreasing in size distally with one or two below first flowers; those bracts subtending flowers protruding at nearly a 90 degree angle from scape; concaved supporting flower bud; lowest bracts resembling sessile leaves with largest 3.05 cm long 1.0 cm wide and smallest bracts 1.0 cm long and about 0.5 cm wide; with variegated margins resembling leaves of about 1.0 to 3.0 mm wide.

*Scape bract color.*—Adaxial center nearest RHS 144A, adaxial margin nearest RHS 11C; abaxial centers between RHS 138A and RHS 138B, abaxial margins nearest RHS 11C.

Fruit: Ti-loculicidal capsule, about 4.0 cm long and 5 mm diameter; between RHS 139B and RHS 141B as ripening.

Seed: Flattened single-winged nutlet with swollen embryo at one end; about 10 mm long, 3 mm wide and 1 mm thick at embryo; nearest RHS 202A.

Disease resistance: The new plant has not shown any resistance to pests and diseases common to *Hostas*. The plant grows best and shows best coloration with plenty of moisture, adequate drainage and light shade, but is able to tolerate some drought when mature and direct sun without leaf burn when provided sufficient water. Hardiness at least from USDA zone 3 through 9, and other disease resistance is typical of that of other *Hostas*.

I claim:

1. A new and distinct ornamental plant cultivar named *Hosta* 'Wheee!' as herein described and illustrated, comprising emerging shoots with broad intensely-sinuate bracts or intermediate leaves partially clasping and surrounding emerging shoots petioles and expanding leaves, with intensely-sinuate elliptic leaves having yellow margins, leaf blade centers of light green, light lavender flowers on strongly erect scapes suitable as a potted plant, for the garden, and for cut flower or cut foliage arrangements.

* * * * *